(12) United States Patent
Ohtsuka et al.

(10) Patent No.: US 7,772,457 B2
(45) Date of Patent: Aug. 10, 2010

(54) MANUFACTURING METHOD OF ABSORBENT BODY AND ABSORBENT BODY FOR DISPOSABLE DIAPER OBTAINED BY THE METHOD

(75) Inventors: Yoji Ohtsuka, Shikokuchuo (JP); Isao Mori, Shikokuchuo (JP)

(73) Assignee: Daio Paper Corporation, Ehime (JP)

( * ) Notice: Subject to any disclaimer, the term of this patent is extended or adjusted under 35 U.S.C. 154(b) by 657 days.

(21) Appl. No.: 10/580,287

(22) PCT Filed: Nov. 24, 2004

(86) PCT No.: PCT/JP2004/017392

§ 371 (c)(1),
(2), (4) Date: May 24, 2006

(87) PCT Pub. No.: WO2005/051274

PCT Pub. Date: Jun. 9, 2005

(65) Prior Publication Data

US 2007/0129699 A1     Jun. 7, 2007

(30) Foreign Application Priority Data

Nov. 25, 2003 (JP) ............................ 2003-394360

(51) Int. Cl.
*A61F 13/15* (2006.01)
*A61F 13/20* (2006.01)

(52) U.S. Cl. ...................................... 604/380; 604/379
(58) Field of Classification Search ......... 604/378–383, 604/385.01, 385.101
See application file for complete search history.

(56) References Cited

U.S. PATENT DOCUMENTS 3,221,738 A * 12/1965 Ekberg et al. ................ 604/366

(Continued)

FOREIGN PATENT DOCUMENTS

EP    0 238 334 A1    9/1987

(Continued)

OTHER PUBLICATIONS

Chinese Office Action (and English translation thereof) dated Apr. 25, 2008, issued in a counterpart Chinese Application.

(Continued)

*Primary Examiner*—Michele Kidwell
(74) *Attorney, Agent, or Firm*—Frishauf, Holtz, Goodman & Chick, P.C.

(57) ABSTRACT

A pair of rollers 2 and 3 are provided to be opposed to each other with a predetermined distance wherein at least one of the rollers 2 and 3 is a press print processing roller 2 that has a plurality of processing projections 2a with a predetermined layout on a circumference surface, and a stripe-shaped absorbent body base 1 including an absorbent element 7 obtained by mixing at least pulp 8 with super absorbent polymer 9 is sent and transferred between the pair of rollers 2 and 3 so that at least one surface of the absorbent body base 1 has a plurality of linear pattern elements 1a provided by being squeezed by the processing projections 2a, so as to have a groove-like shape when seen from the top, and are individually spaced from one another and dispersed in a staggered manner.

7 Claims, 9 Drawing Sheets

U.S. PATENT DOCUMENTS

| | | | |
|---|---|---|---|
| 3,908,659 A | | 9/1975 | Wehrmeyer et al. |
| 4,333,979 A | * | 6/1982 | Sciaraffa et al. ............ 428/179 |
| 4,443,512 A | * | 4/1984 | Delvaux .................... 428/162 |
| 4,518,451 A | | 5/1985 | Luceri et al. |
| 5,030,500 A | * | 7/1991 | Perdelwitz et al. .......... 428/137 |
| 5,038,989 A | | 8/1991 | Beliveau |
| 5,069,676 A | * | 12/1991 | Ito et al. .................... 604/380 |
| 5,925,026 A | * | 7/1999 | Arteman et al. ............. 604/383 |
| 2003/0139719 A1 | | 7/2003 | Nanaumi et al. |
| 2004/0253892 A1 | | 12/2004 | Baker et al. |
| 2005/0182374 A1 | * | 8/2005 | Zander et al. ............... 604/380 |

FOREIGN PATENT DOCUMENTS

| | | |
|---|---|---|
| EP | 0 293 208 A | 11/1988 |
| EP | 1 330 995 A | 7/2003 |
| EP | 1 633 295 B | 9/2008 |
| GB | 1236904 A | 6/1971 |
| JP | 57-069856 A | 4/1982 |
| JP | 59-64043 A | 4/1984 |
| JP | 59-124524 U | 8/1984 |
| JP | 60-189505 U | 12/1985 |
| JP | 61-028002 A | 2/1986 |
| JP | 61-048359 A | 3/1986 |
| JP | 61-191359 A | 8/1986 |
| JP | 62-221348 A | 9/1987 |
| JP | 63-027405 U | 2/1988 |
| JP | 3-030934 A | 2/1991 |
| JP | 05-300922 A | 11/1993 |
| JP | 11-89880 A | 4/1999 |
| JP | 2001-008971 A | 1/2001 |
| JP | 2001-129018 A | 5/2001 |
| JP | 2003-033397 A | 2/2003 |
| JP | 2003-039581 A | 2/2003 |
| JP | 2003-265519 A | 9/2003 |
| WO | WO 03/000162 A | 1/2003 |

OTHER PUBLICATIONS

Notification Concerning Transmittal of International Preliminary Report on Patentability, Chapter I of the Patent Cooperation Treaty for PCT/JP2004/017392, and Written Opinion, 5 sheets.

Chinese Office Action dated Mar. 20, 2009 (6 pages), and English translation thereof (5 pages), issued in counterpart Chinese Application Serial No. 2004800349021.

Supplementary European Search Report dated Jun. 30, 2009 issued in a counterpart European Application No. 04 81 9358.

Japanese Office Action dated Dec. 16, 2008 (2 pages), and English translation thereof (4 pages) issued in counterpart Japanese Application No. 2003-394360.

Information Statement (6 pages) and English translation thereof (18 pages) submitted Feb. 19, 2008 in counterpart Japanese Application No. 2003-394360.

* cited by examiner

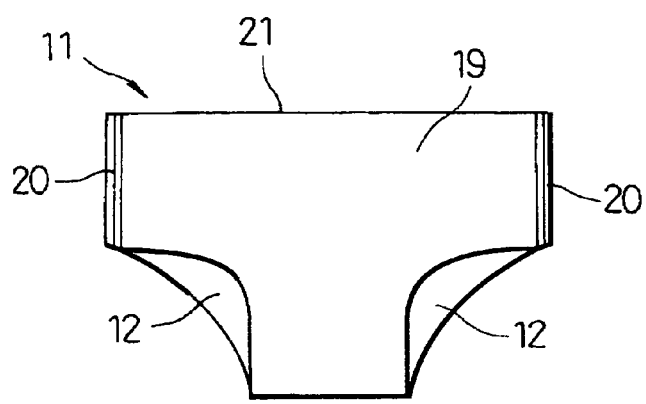
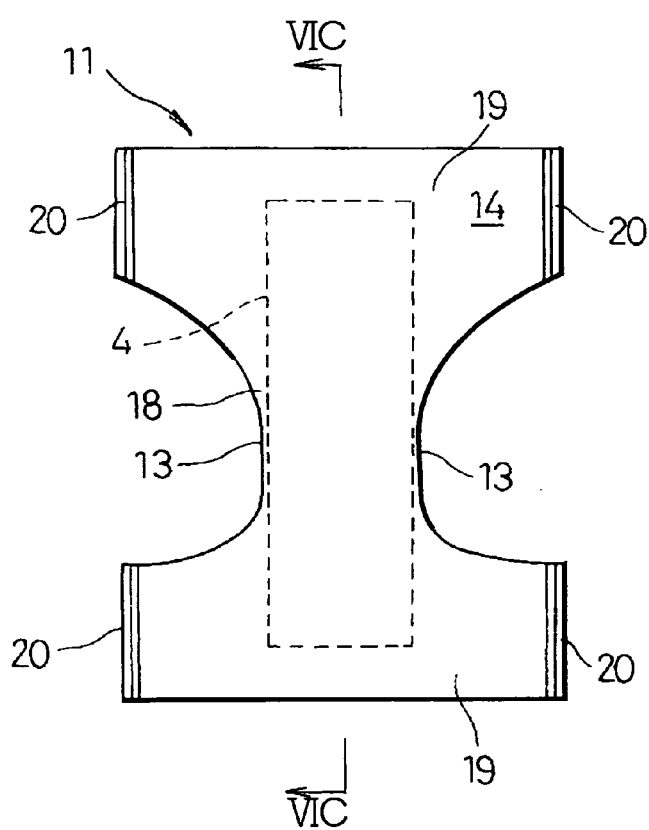
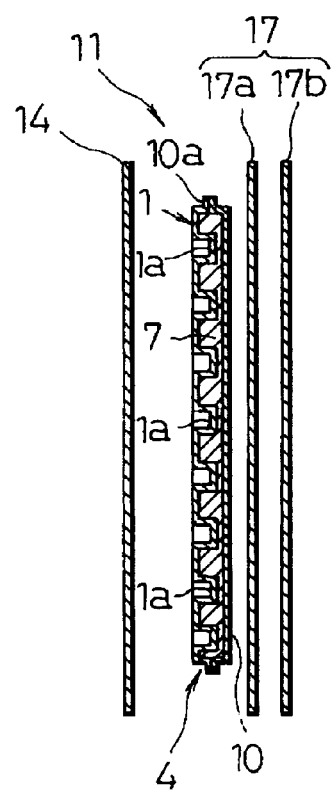

MANUFACTURING METHOD OF ABSORBENT BODY AND ABSORBENT BODY FOR DISPOSABLE DIAPER OBTAINED BY THE METHOD

This application is a U.S. National Phase Application under 35 USC 371 of International Application PCT/JP2004/017392 filed Nov. 24, 2004.

FIELD OF THE INVENTION

The present invention mainly relates to a method by which an absorbent body can be preferably manufactured that absorbs urine and stool in a disposable diaper, and a disposable absorbent body obtained by this manufacturing method.

DESCRIPTION OF THE BACKGROUND

In recent years, disposable diapers have been widely used for the nursing care of babies as well as bedfast old people and patients. This disposable diaper is roughly classified into the flat-type one that requires a diaper cover and that has a rectangular flat plate-like shape and the pants-type one that does not require a diaper cover. These diapers basically have a trilaminar structure in which an absorbent body is provided between an outer face sheet, whose outer face of a liquid-impermeable sheet is adhered with a nonwoven fabric, and an inner face sheet consisting of a liquid-permeable sheet. The absorbent body is structured so that an absorbent element obtained by mixing flocculation pulp with super absorbent polymer is filled into a liquid-permeable storage bag consisting of a nonwoven fabric sheet. When the absorbent body is used in a disposable diaper, urine or highly-flowable stool is absorbed by the super absorbent polymer and swells, thus allowing the urine or stool to be accepted and retained in the absorbent body.

The above absorbent body is formed, for the purpose of accepting and retaining a large amount of urine and stool as much as possible, by preparing an absorbent body base with a slightly large amount of the absorbent element filled in a storage bag, and sending this absorbent body base through a pair of press rollers having flat pressing faces so that this absorbent body base is pressed flat, thereby providing the absorbent body having a predetermined thin thickness. The reason why the absorbent body is formed to have such a thin thickness is for the purpose of improving the wearing feeling of a disposable diaper when the disposable diaper is worn by a user and for improving the binding power between pulp and super absorbent polymer in the absorbent element to provide strength, by which the disposable diaper can be prevented from losing its shape when the disposable diaper absorbs urine and stool.

On the other hand, another diaper absorbent body other than the above one has been suggested in which an absorbent body base includes a plurality of straight embossed patterns that are inclined toward the center so that a plurality of pattern rows are arranged in the longitudinal direction of a rectangle shape (see Patent Reference 1 for example).

Patent Reference 1: Japanese Patent Unexamined Publication No. 5-300922

DISCLOSURE OF THE INVENTION

Problem to be Solved by the Invention

However, in the case of the former absorbent body, which is formed through the process for reducing the thickness thereof, the entire absorbent body base is squeezed so as to have the substantially same thickness. Thus, this squeezing step cannot apply a high linear pressure (a pressing force per a unit length applied from the rollers to the absorbent body base) and generally squeezes an absorbent body base with a relatively low linear pressure of approximately 0.71 to 1.79 kgf/cm. Therefore, as time passes, the absorbent body formed through the above squeezing step returns to have an original thick thickness due to the restoring force of the absorbent element. This deteriorates the binding power between the pulp and the super absorbent polymer in the absorbent element, resulting in a lowered strength.

Furthermore, in the step for reducing the thickness of the absorbent body base, the absorbent body base is squeezed by pressing, the entire width of the absorbent body base perpendicular to a direction along which the base is sent, with the flat pressing faces of the pair of press rollers. This causes, despite of the relatively low linear pressure as described above, a difficulty in that the pressed absorbent body base adheres to an extent that it cannot be easily peeled off from the press rollers. As a result, an inconvenience may be caused where the absorbent body base sent through the pair of press rollers is wound around the press roller and thus cannot be sent smoothly. This is one of the causing factors that deteriorate the quality and productivity of the absorbent body.

Furthermore, the absorbent body manufactured by the above process may have another inconvenience in that the entire squeezed body may become too hard due to an unfavorable shape such as warpage. In addition, the absorbent body manufactured by the above process merely has the entire face squeezed and thus has an appearance that is far from a good design.

Furthermore, due to the entire absorbent body base being squeezed, the above absorbent body has the pulp and the super absorbent polymer in the absorbent element that are mixed too closely. This prevents, when the super absorbent polymer absorbs water in particular, the super absorbent polymer from sufficient swelling, which deteriorates the absorption property.

On the other hand, in the case of the latter absorbent body in which a plurality of embossed pattern rows are formed, the absorbent body base includes a pattern of convex-shaped embossed pattern elements in which the respective neighboring two embossed pattern elements have therebetween a liquid dispersion path. Thus, a major area of the absorbent body base other than an area where the embossed pattern elements are formed is pressed. Specifically, the embossed pattern is formed by rolling the absorbent body base by embossing rollers including a plurality of linear processing recess frames at the circumference surface thereof. Thus, the substantial entire absorbent body base is squeezed by the rollers, causing a similar problem as that of the former absorbent body. Furthermore, the number of embossed pattern elements in the embossed pattern on a straight line in the width direction that is orthogonal to the longitudinal direction of the absorbent body base is different depending on each line in the above longitudinal direction. This causes, when the embossed pattern is formed in an absorbent body base, the pressure applied from the embossing roller to the absorbent body base to be changed depending on the difference in the number of formed embossed pattern elements in the embossed pattern. This pressure variation causes corresponding vibration in the roller, causing another problem where an embossed pattern having a predetermined shape cannot be formed in a stable manner.

In view of the above conventional problems, it is an objective of the present invention to provide a method for providing, with high productivity and in a smooth manner, an absorbent body structured so that an absorbent element can maintain an intended absorption performance while having a predetermined strength, and a favorable disposable diaper absorbent body obtained by this method.

Means to Solve the Problem

According to a first aspect of the invention a manufacturing method for manufacturing an absorbent body is provided, wherein: a stripe-shaped absorbent body base, including an absorbent element obtained by mixing at least pulp with super absorbent polymer, is sent and transferred through a pair of rollers that are provided to be opposed to each other with a predetermined distance, wherein at least one of the rollers is a press print processing roller that has a plurality of processing projections with a predetermined layout on a circumference surface; and a plurality of linear pattern elements are formed on at least one surface of the absorbent body base, wherein the linear pattern elements are formed by being squeezed by the processing projections so as to have a groove-like shape when seen from the top, and the plurality of linear pattern elements are individually spaced from one another and dispersed in a staggered manner.

According to a second aspect of the invention, the linear pattern elements are arranged so that number of the linear pattern elements on any of straight line that extend in a width direction orthogonal to a transfer direction of the absorbent body base is equal, and so that the linear pattern elements have a fixed distance thereamong in the width direction.

According to a third aspect of the invention, the linear pattern elements are formed in a linear shape so that an orientation angle, which is a degree of inclination of the linear pattern elements to the transfer direction of the absorbent body base, is 50 degrees or less at any portion.

According to a fourth aspect of the invention: the absorbent element is filled into a storage bag obtained by sealing edge parts of a liquid-permeable sheet of the absorbent body base provided with the linear pattern elements; the plurality of linear pattern elements having a linear groove shape when being seen from the top are arranged to have spaces thereamong in a dispersed and staggered manner while the absorbent element is squeezed until its absorption performance almost disappears; and an area in the absorbent body base in which the linear pattern elements are not formed have a predetermined thickness.

According to a fifth aspect of the invention, the absorbent body base used for disposable diaper has an inner surface that is adhered with a liquid diffusion sheet and the plurality of linear pattern elements are formed concavely, together with the liquid diffusion sheet, in the inner surface of the absorbent body base.

According to a sixth aspect of the invention, the plurality of linear pattern elements are formed concavely on both faces of the absorbent body base so as to be opposed to one another with the same layout.

Effect of the Invention

The invention according to the first aspect arranges, in a staggered and dispersed manner, linear pattern elements having a linear groove-like shape when being seen from the top. Thus, these linear pattern elements occupy a very small proportion of the entire surface area of the absorbent body base. Thus, a major area of the absorbent element except for the area in which the linear pattern elements are formed has a thickness that is slightly reduced to a predetermined thickness and the absorbent element is prevented from being crushed, thus an intended absorption performance is secured. Thus, the entire absorbent element has an absorption capability that is not so much deteriorated. Therefore, the absorbent body formed in this manner has a strength which enables, by the strongly-squeezed linear pattern elements, an area in the absorbent body base having no linear pattern elements to be prevented from returning into a thickness before the squeezing process and simultaneously allows the absorbent element in the major area of the absorbent body base having no linear pattern elements to securely maintain an intended absorption performance. Thus, a resulting disposable diaper can have a sufficient absorption performance while having a required strength. Specifically, a conventional process to provide an absorbent body by squeezing entirely or substantially entirely an absorbent body base, can squeeze the absorbent body base only with a relatively small linear pressure. In contrast to this, this absorbent body can provide a required absorption performance by the major area of the absorbent body base having no linear pattern elements. Thus, no problem is caused even when the linear pattern elements are strongly squeezed until the absorption performance almost disappears.

The invention according to the second aspect can always retain a fixed linear pressure applied from the press print processing roller to the stripe-shaped absorbent body base in the width direction and can arrange the respective linear pattern elements in a discontinuous and dispersed manner so as to have a distance thereamong. Thus, a relatively-high linear pressure can be uniformly applied to the respective processing projections of the press print processing roller in a dispersed manner. As a result, the press print processing roller is prevented from having vibration due to the change in the pressure. Thus, the press print processing roller can be always driven and rotated in a stable manner.

Even when the absorbent body base is squeezed by a relatively-high linear pressure applied from the press print processing roller, the invention according to the third aspect prevents increase in resistance force that is caused when the absorbent body base is sent after the absorbent body base 1 is squeezed by the processing projection. On the other hand, when the orientation angle θ is 50 degrees or more, the absorbent body base 1 may have a high resistance force when the linear pattern elements are separated from the processing projection, which may cause a scratch at the edge part of the formed linear pattern elements. The above resistance that is prevented from being increased also prevents a difficulty in that the formed linear pattern elements adheres to the processing projection to an extent that it cannot be easily peeled off from the processing projection. This eliminates an inconvenience where the absorbent body base sent through the pair of rollers is wound around, thus allowing the absorbent body base to be smoothly transferred. Thus, the linear pattern elements can be formed by smoothly transferring the absorbent body base.

The invention according to the fourth aspect allows a major area of the absorbent body base to have no linear pattern elements. Thus, super absorbent polymer in this area having no linear pattern elements holds an intended absorption performance to efficiently absorb liquid and significant swelling. During this time, the plurality of linear pattern elements arranged in a uniform and staggered manner provide high strength, by which the resultant disposable diaper is securely prevented from losing or having biased shape. Furthermore, the respective two neighboring linear patterns provide a function as a dispersion path through which absorbed urine or stool having high flowability is dispersed. This allows the urine or stool to be guided by the linear pattern elements so that the urine or stool is appropriately dispersed in the absorbent body in longitudinal and lateral directions, thereby being uniformly absorbed by the entire absorbent body.

The invention according to the fifth aspect allows the liquid diffusion sheet covering the inner surface of the absorbent body base to provide a capillary phenomenon through which urine is dispersed over the entire surface. As a result, a situation is prevented where only the super absorbent polymer at a particular part of the absorbent body to have an excessive amount of urine and excessively swell.

The invention according to the sixth aspect can provide a further higher strength by the respective pairs of linear pattern elements that are formed in both surfaces of the absorbent body base so as to be opposed to one another.

BRIEF DESCRIPTION OF THE DRAWINGS

FIG. 6A This is a front view schematically illustrating the structure outline of a disposable diaper structured by the disposable diaper absorbent body obtained by the manufacturing method.

FIG. 6B This is a development view schematically illustrating the structure outline of a disposable diaper structured by the disposable diaper absorbent body obtained by the manufacturing method.

FIG. 6C This is an exploded cross sectional view cut by line VIC-VIC.

BEST MODE FOR CARRYING OUT THE INVENTION

Figure 1:
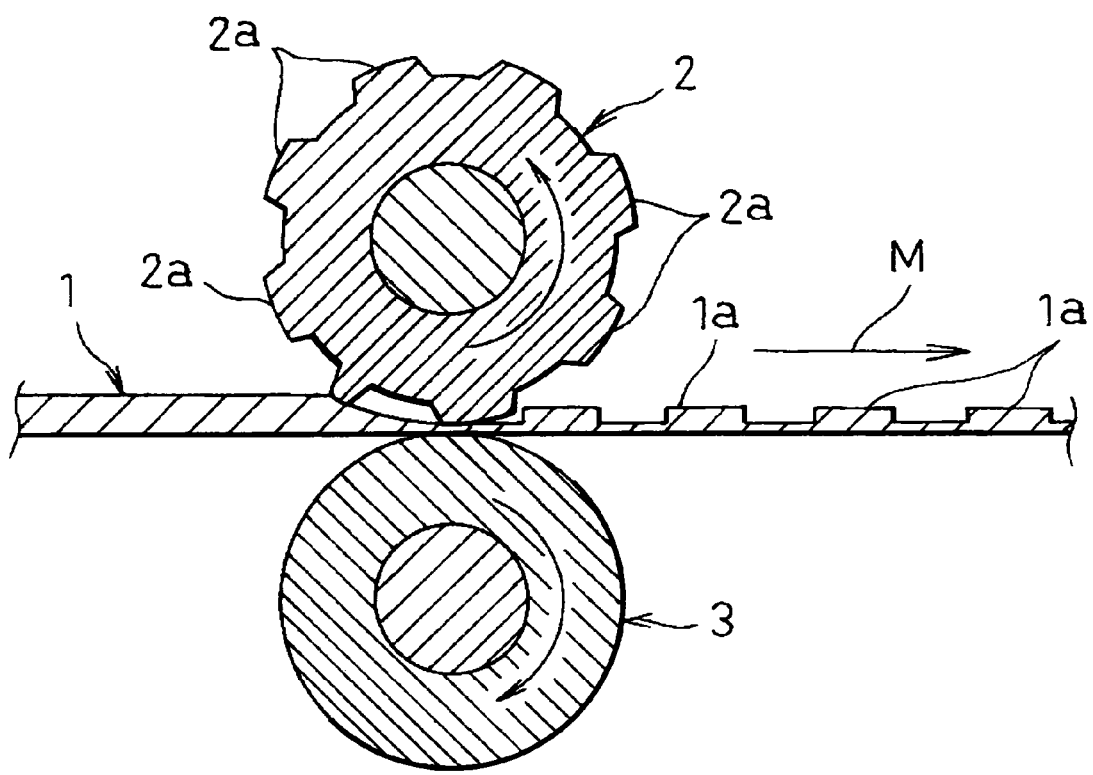
FIG. 1 This is a schematic longitudinal sectional view illustrating an absorbent body manufacturing apparatus that embodies a manufacturing method of an absorbent body according to the first embodiment of the present invention.
Figure 2:
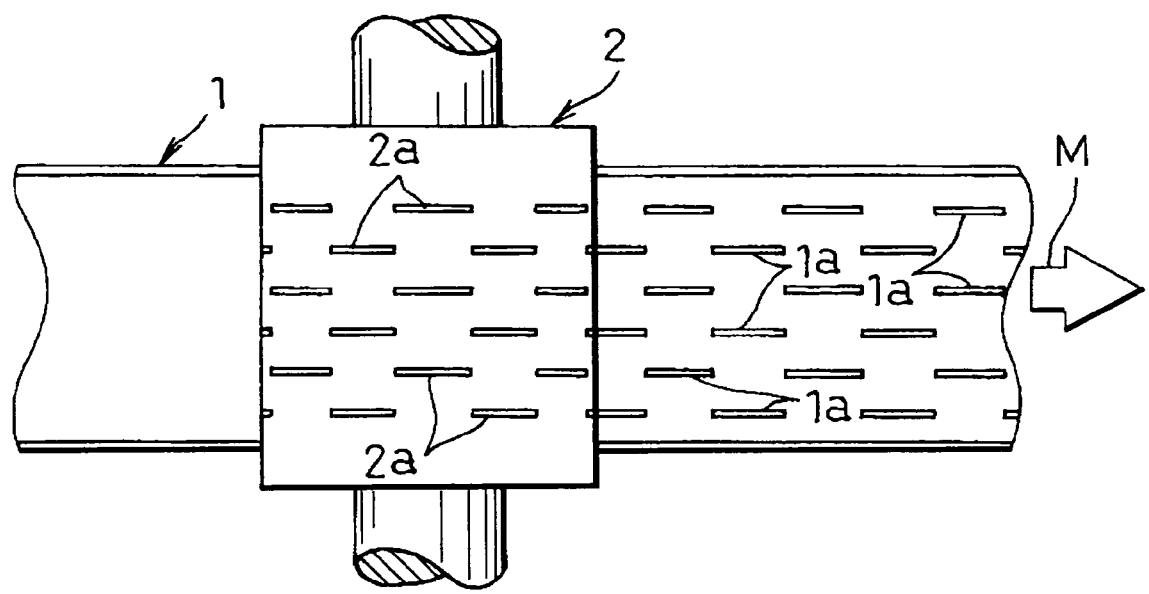
FIG. 2 This is a plane view illustrating the absorbent body manufacturing apparatus.

Hereinafter, preferred embodiments of the present invention will be described with reference to the drawings. FIG. 1 is a schematic longitudinal sectional view illustrating an absorbent body manufacturing apparatus that embodies a manufacturing method of an absorbent body according to the first embodiment of the present invention. FIG. 2 is a plane view illustrating the manufacturing apparatus. This manufacturing apparatus includes an embossing roller 2 and a backup plain roller 3 that are provided at the upper and lower position with a predetermined interval therebetween. In the embossing roller 2, processing projections 2a protruding linearly are formed on the circumference surface with a predetermined layout. The backup plain roller includes a flat circumference surface. These rollers 2 and 3 are driven and rotated in a synchronized manner or only the embossing roller 2 is driven and rotated in the direction shown by the arrow. In this manufacturing method, the absorbent body base 1 is moved while being sandwiched by the above rollers 2 and 3 to reduce the thickness of the absorbent body base to a predetermined thickness and to form linear pattern elements 1a on one face (upper face of FIG. 1) that are provided concavely by squeezing by the processing projection 2a. Details of the absorbent body base 1 will be described later.

Figure 3A:
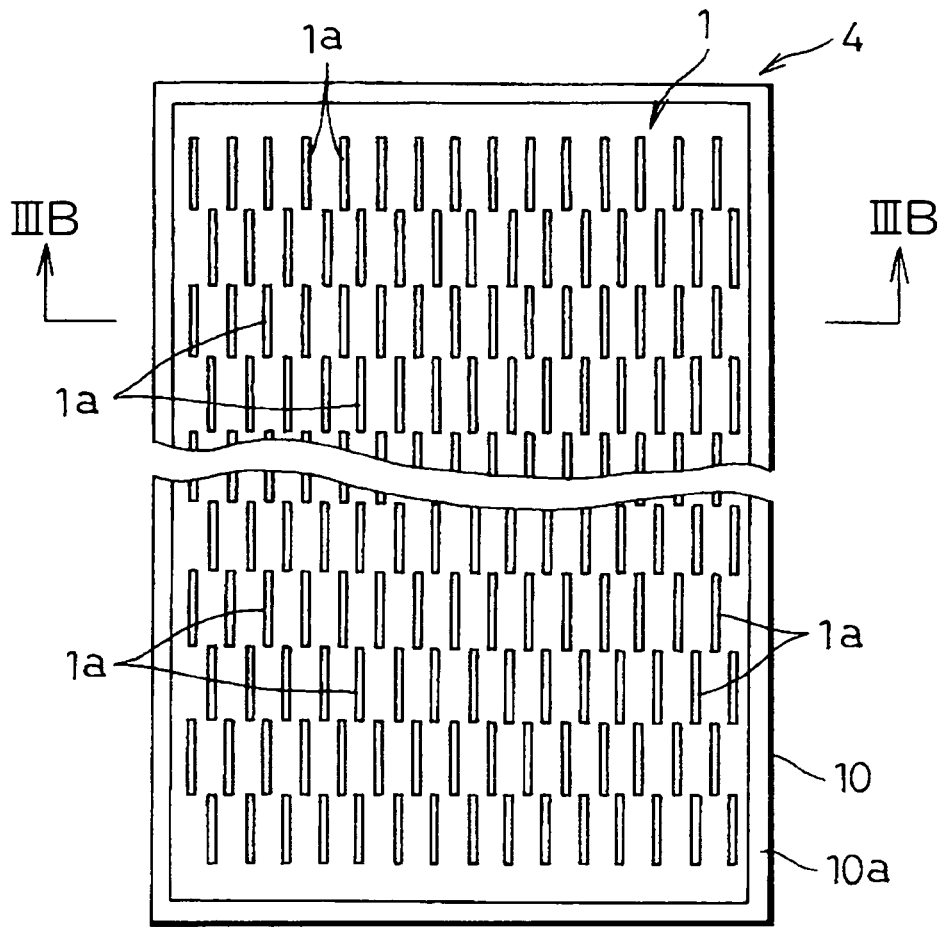
FIG. 3A This is a plan view illustrating a partially fractured absorbent body for disposable diaper obtained by the manufacturing method.
Figure 3B:
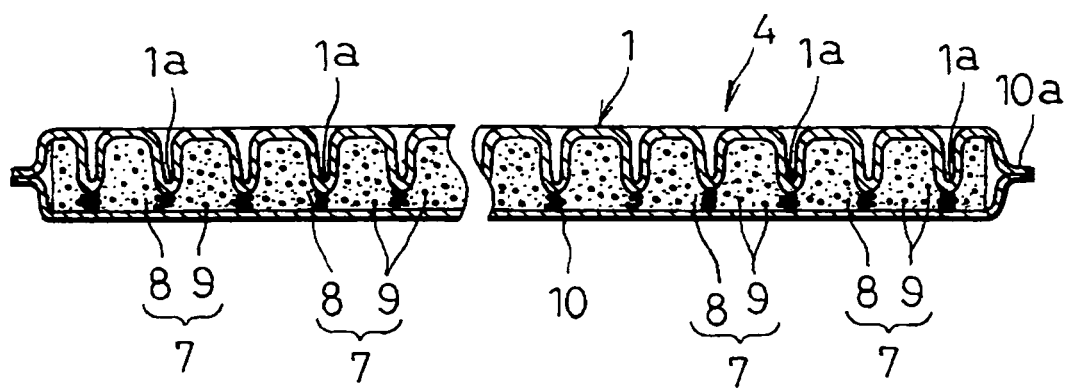
FIG. 3B This is a frame format of cross sectional view illustrating the interior of a portion cut by line IIIB-IIIB of FIG. 3A.

FIG. 3A is a plane view illustrating a partially fractured absorbent body 4 for disposable diaper obtained by the above-described manufacturing method. FIG. 3B is a frame format of cross sectional view illustrating the interior of a portion cut by the line IIIB-IIIB of FIG. 3A. This absorbent body 4 for disposable diaper is obtained by using the above-described step to form, in one face of the absorbent body base 1, linear pattern elements 1a with a predetermined layout, then subsequently cutting the obtained absorbent body base 1 to have a predetermined size, and finally adhering the cut portions, thereby forming a sealed portion 10. The absorbent body 4 for disposable diaper has a flat appearance when seen from the top.

As shown in FIG. 3B, the above absorbent body base 1 has a structure in which absorbent element 7 is provided by mixing flocculation pulp 8 with super absorbent polymer 9, and then storing and sealing it in a storage bag 10. The above storage bag 10 is provided by overlapping two liquid-permeable sheets consisting of nonwoven fabric or the like or folding one liquid-permeable sheet in the middle so that the edge portion thereof can be sealed at a sealed portion 10a. Super absorbent polymer 9 which mainly composes the absorbent element 7 has a high absorption performance by which the super absorbent polymer 9 absorbs, while swelling, water of a volume that is 20 to 30 times of the volume of the super absorbent polymer 9.

As schematically illustrated in FIG. 3B in an easy-to-understand manner, the above disposable diaper absorbent body 4 is pressed until the absorption performance at positions at which the linear pattern elements 1a are formed in the absorbent element 7 almost disappears. Any of these linear pattern elements 1a is straight, having a single predetermined length. These linear pattern elements 1a are formed so that they are dispersed to provide a staggered arrangement. Thus, these linear pattern elements 1a occupy a very small proportion of the entire surface area of the absorbent body base 1. This allows the entire absorbent element 7 to have little decrease in the absorption capability because the major area of the absorbent element 7 except for an area in which the linear pattern elements 1a are formed has a predetermined slightly reduced thickness and the super absorbent polymer 9 maintains an intended absorption performance within being pressed in a very small amount.

Specifically, by the strongly squeezed linear pattern elements 1a, the above absorbent body 4 for disposable diaper has a strength by which an area in the absorbent body base 1 having no linear pattern elements 1a is prevented from having an original thickness and simultaneously allows the absorbent element 7 in a major area of the absorbent body base 1 having no linear pattern elements 1a to securely maintain an intended absorption performance. Thus, the absorbent body 4 for disposable diaper can maintain a sufficient absorption performance while having a predetermined strength. In other words, while a conventional process for providing an absorbent body by squeezing entirely or substantially entirely the absorbent body base, squeezes the absorbent body base only with a relatively low linear pressure, the above absorbent body 4 for disposable diaper can secure a required absorption performance by the major area of the absorbent body base 1 having no linear pattern elements 1a. Thus, the absorbent body 4 for disposable diaper has no problem even when the linear pattern elements 1a are strongly squeezed until the absorption performance almost disappears.

Figure 5:
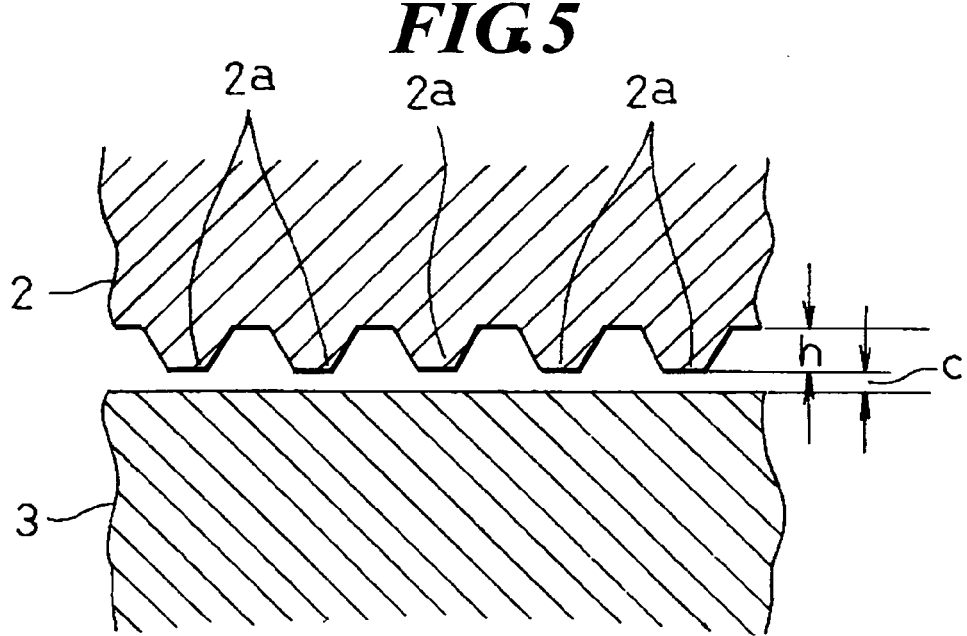
FIG. 5 This is an expanded cross sectional view illustrating the relative positional relation between an embossing roller and a backup plain roller of the absorbent body manufacturing apparatus of FIG. 1.

An example is given hereinafter. The conventional process for squeezing an absorbent body squeezes the absorbent body base with a relatively small linear pressure of 0.71 to 1.79 kgf/cm as described above. In contrast, concerning the above absorbent body 4 for disposable diaper, the absorbent body base 1 is squeezed with a relatively high linear pressure of 5.56 to 13.89 kgf/cm to form the linear pattern elements 1a. When the thickness of the absorbent body base 1 before being squeezed by the rollers 2 and 3 is 6.0 to 10.0 mm and when a protrusion height h of the processing projection 2a of the embossing roller 2 is 0.5 to 2.5 mm and a clearance c between the processing projection 2a and a receiving face of the backup plain roller 3 is 0.15 to 0.5 mm as shown in FIG. 5, a linear pressure applied from the embossing roller 2 to the absorbent body base 1 can be set to have 5.56 to 13.89 kgf/cm as described above, to provide the linear pattern elements 1a having a high strength and to allow an area of the absorbent body base 1 having no linear pattern elements 1a to have a required thickness of 3 mm or less.

As described above, when a relatively-high linear pressure is applied to the absorbent body base 1 to form the linear pattern elements 1a, consideration must be paid so that, without causing the embossing roller 2 to have a high load resistance, the rollers 2 and 3 can be stably driven and rotated and the absorbent body base 1 can be smoothly sent from the rollers 2 and 3. To solve this problem, the above manufacturing method takes measures as described below.

Figure 4:
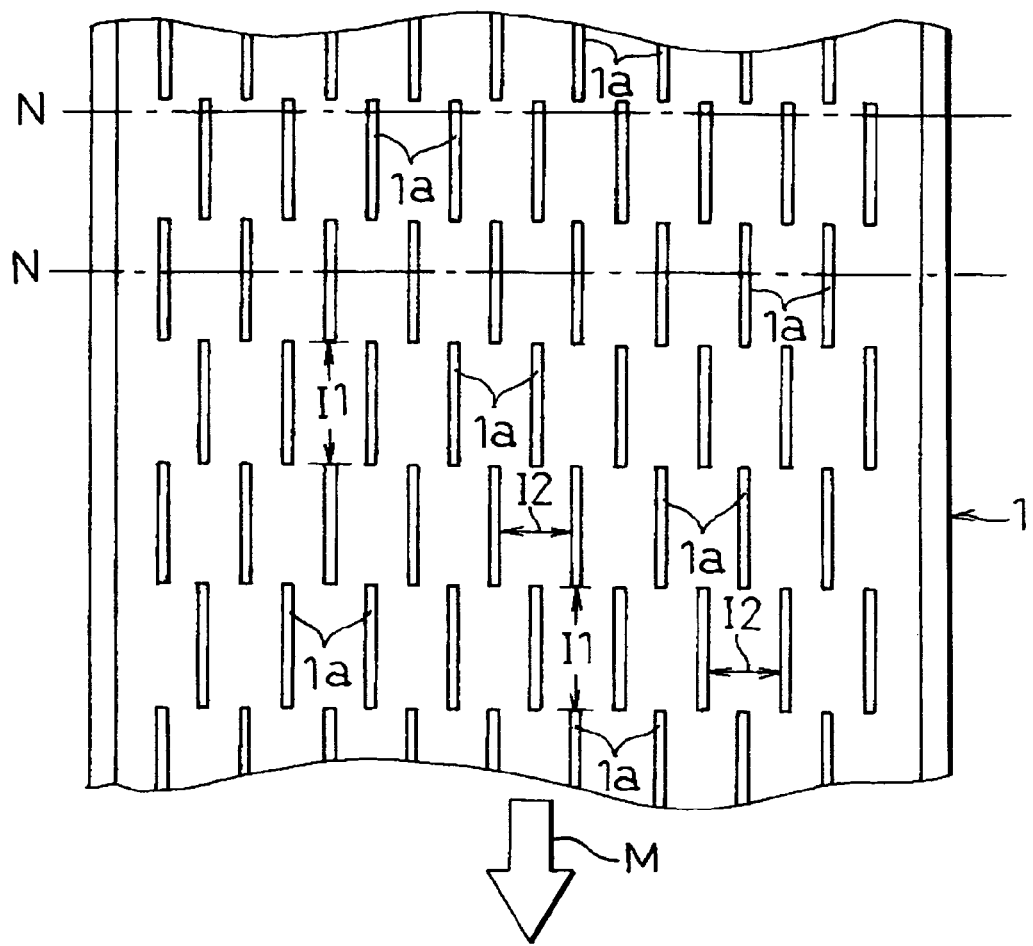
FIG. 4 This is an expanded top view illustrating an absorbent body base in which linear pattern elements are formed by the manufacturing apparatus.

Specifically, the above manufacturing method provides the respective linear pattern elements 1a as shown in FIG. 4 so that the number of the linear pattern elements 1a arranged on any of the straight lines N that extend in the width direction orthogonal to a transfer direction M, along which the absorbent body base 1 is transferred from the rollers 2 and 3, is equal (which is 9 in this embodiment). As a result, a linear pressure applied from the embossing roller 2 to the width direction of the absorbent body base 1 is always maintained to be uniform.

Furthermore, the above manufacturing method also forms the respective linear pattern elements 1a so that two neighboring linear pattern elements 1a in the transfer direction M are spaced to have a fixed distance I1 therebetween and so that two neighboring linear pattern elements 1a in the above width direction are spaced to have a fixed distance I2 therebetween. Thus, the above-described relatively high linear pressure of 5.56 to 13.89 kgf/cm can be applied to the individual processing projections 2a in a uniform and dispersed manner. As a result, the embossing roller 2 can be always driven and rotated without having vibration due to the variation in pressure because the above-described linear pressure applied in the width direction of the absorbent body base 1 is always maintained to be uniform.

Furthermore, the respective linear pattern elements 1a are formed in a direction that is parallel with the transfer direction M of the absorbent body base 1 (i.e., in a direction, in which an orientation angle θ to the transfer direction M is 0 degree). As a result, in spite of the relatively high linear pressure applied from the embossing roller 2 to the absorbent body base 1 to squeeze the absorbent body base 1, resistance force when sending the absorbent body base 1 by the processing projections 2a after squeezing the absorbent body base 1 is prevented from being increased. Specifically, when a value of the above orientation angle θ is 50 degrees or higher, a high resistance force is generated to the absorbent body base 1 when the linear pattern elements 1a are separated from the processing projections 2a, which may cause a scratch at an edge of the linear pattern element 1a after forming. Furthermore, by setting the linear pressure to the above-described 5.56 to 13.89 kgf/cm, the linear pattern elements 1a after forming can be smoothly separated from the processing projection 2a. Specifically, when the linear pressure is 13.89 kgf/cm or higher, the linear pattern element 1a after forming may jump out of the processing projection 2a, which may cause a scratch at an edge of the linear pattern element 1a.

Furthermore, the respective linear pattern elements 1a are dispersed in a discontinuous manner to have fixed distances of I1 and I2 thereamong in the transfer direction M and in the width direction N. Thus, with the above-described orientation angle θ that is set to 50 degrees or lower so as to prevent high resistance, the linear pattern element 1a after forming is prevented from being closely attached to the processing projection 2a to an extent at which the linear pattern element 1a after forming cannot be peeled off from the processing projection 2a. This eliminates a risk where the absorbent body base 1 that passed through the rollers 2 and 3 is wound around the embossing roller 2, thus allowing the absorbent body base 1 to be always transferred smoothly. Thus, the above manufacturing method can manufacture the absorbent body 4 for disposable diaper having a high quality with high productivity.

FIG. 6A is a front view schematically illustrating the structure outline of the disposable diaper 11 structured by the absorbent body 4 for disposable diaper obtained by the above manufacturing method. FIG. 6B is a development view of the disposable diaper 11. FIG. 6C is an exploded cross sectional view cut by the line VIC-VIC of FIG. 6B. When it is developed, this disposable diaper 11 has an entirely rectangular shape. At both sides of the rectangular shape, curved cutout portions 13 are provided for the purpose of providing leg openings 12. The curved cutout portions 13 are provided to an inner face sheet 14 that consists of a liquid-permeable sheet (e.g., nonwoven fabric). An outer face sheet 17 that has the same shape as that of the inner face sheet 14 is provided by adhering an outer face of a liquid-impermeable sheet 17a (e.g., polyethylene sheet) with a nonwoven fabric 17b so that the outer face sheet 17 has a cloth-like feeling. The inner face sheet 14 and the outer face sheet 17 have therebetween the absorbent body 4 for disposable diaper obtained by the above-described manufacturing method. The absorbent body 4 for disposable diaper has a rectangle appearance longitudinally extending between body peripheral portions 19 to have substantially the same width as that of a crotch portion 18 between the curved cutout portions 13.

As described with reference to FIG. 3B, the absorbent body 4 has a structure in which the storage bag 10 is filled with the absorbent element 7 provided by mixing the pulp 8 with the super absorbent polymer 9 that has a very high moisture absorption property so as to absorb water of a volume 20 to 30 times the volume of itself when swelling, thereby constituting a urine absorption region of this disposable diaper 11. This disposable diaper 11 has a pants-like shape as shown in FIG. 6A in which the upper part has a body opening portion 21 by the body peripheral portions 19 and the lower part has the leg openings 12 at both sides thereof. This pants-like shape is provided by sandwiching the absorbent body 4 with the inner face sheet 14 and the outer face sheet 17 adhering the laminated members to one another to provide an integrated sheet-like structure. Then, this integrated sheet-like structure is folded at the center in the longitudinal direction and then the welded portions 20 except for the curved cutout portion 13 are adhered to each other.

Although not shown, the body peripheral portion 19 is embedded with elastic material (e.g., rubber) so that the body opening portion 21 can be made fit to the body of a user. The leg opening 12 also includes a three-dimensional gather portion to prevent urine or stool from leaking from a space between the leg opening 12 and a leg of a user. This three-dimensional gather portion is provided, for example, by folding a liquid-permeable sheet to have a U-shaped cross sections so that the inner side has a liquid-impermeable sheet. Then, the edge of a face of the body peripheral sheet including a plurality of string rubbers with an appropriate distance thereamong is adhered with the adhesion portion of the side edge of the inner face sheet 14 that is folded so as to wrap around the side edge of the outer face sheet 17 and the absorbent body 4.

When the disposable diaper 11 having the structure as described above is worn by a user, discharged urine or stool having high flowability permeates the storage bag 10 of the absorbent body 4 and is absorbed by the super absorbent polymer 9 and is stored in the disposable diaper 11 by allowing the super absorbent polymer 9 to absorb the liquid and swell. At this time, in the absorbent body 4 in which a major area of the absorbent body base 1 has no linear pattern elements 1a by the above manufacturing method, the super absorbent body 9 in the above-described area having no linear pattern elements 1a provides an intended absorption performance to efficiently absorb the liquid and significantly swell. During the absorption, the plurality of linear patterns arranged in a staggered manner provide a high strength, thereby securely preventing the disposable diaper 11 from losing or having biased shape. A space between the respective neighboring two linear pattern elements 1a provides a dispersion path through which the absorbed urine or stool having high flowability is dispersed. Thus, the urine or stool is guided by the linear pattern element 1a and is appropriately dispersed in the absorbent body 4 in longitudinal and lateral directions and is uniformly absorbed by the entire absorbent body 4. Furthermore, this disposable diaper 11 provides favorable decoration by the plurality of linear pattern elements 1a provided in the absorbent body 4.

Figure 7:
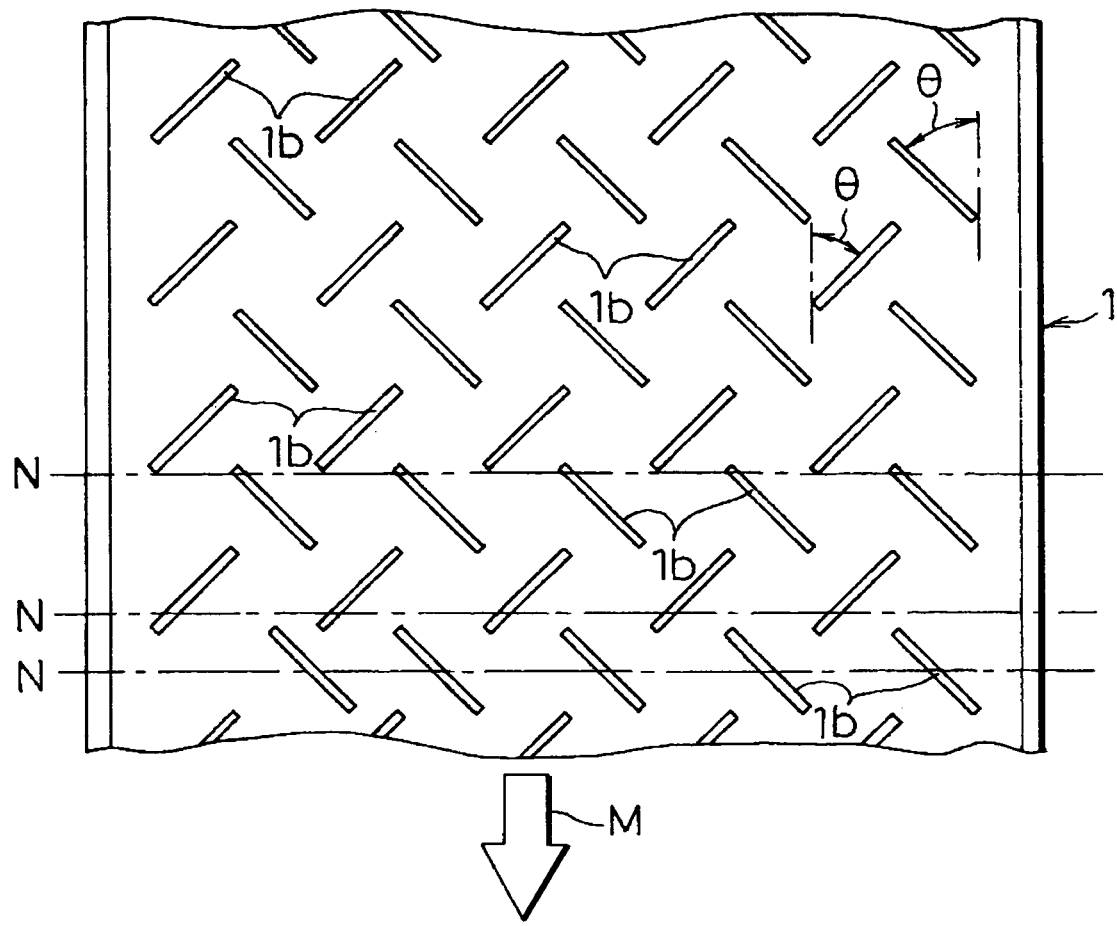
FIG. 7 This is a top view of a process for forming a linear pattern in an absorbent body base by a manufacturing method of an absorbent body according to the second embodiment of the present invention.

FIG. 7 is a top view of a process for forming a linear pattern elements 1b on the absorbent body base 1 by a manufacturing method of an absorbent body according to the second embodiment of the present invention. The manufacturing method of this embodiment is different from that of the first embodiment only in that the plurality of linear straight groove-like pattern elements 1b having a single length provided in the absorbent body base 1 are arranged with a different layout. Specifically, the plurality of linear pattern elements 1b are inclined to either right or left directions with an orientation angle θ of 45 degrees, to the transfer direction M of the absorbent body base 1. Pattern rows of the plurality of linear pattern elements 1b intermittently arranged with the same inclination direction along the transfer direction M to have a fixed distance thereamong are arranged in the width direction orthogonal to the transfer direction M. At the same time, pattern rows having different inclination directions are alternately provided along the width direction and the respective two neighboring pattern rows in the width direction are arranged so that each of the pattern rows is dislocated by a distance between the linear pattern elements 1b neighboring in the transfer direction. In this manner, the linear pattern elements 1b are arranged to show a zigzag pattern by being arranged in a staggered manner in the transfer direction M and in the width direction, respectively.

The embodiment of this manufacturing method also provides an equal number of linear pattern elements 1b in any straight line N in the width direction (the number is five in this embodiment). Therefore, linear pressure applied from the embossing roller 2 of FIG. 1 in the above width direction of the absorbent body base 1 is retained to be even. The respective two neighboring linear pattern elements 1b in the width direction are spaced in the same distance so as to be uniformly dispersed in the width direction of the absorbent body base 1. Thus, a relatively-high linear pressure can be uniformly applied to the individual processing projections of an embossing roller. As a result, the embossing roller can be always driven and rotated in a stable manner without generating vibration due to variation of the pressure, since the above-described linear pressure applied from the embossing roller to the absorbent body base 1 in the width direction can be always maintained to be uniform.

Furthermore, the linear pattern elements 1b arranged with the orientation angle θ of 45 degrees to the transfer direction M can prevent, in spite of a relatively high linear pressure applied from the embossing roller to the absorbent body base 1 to squeeze the absorbent body base 1, the absorbent body base 1 from having high resistance when the absorbent body base 1 is sent in the transfer direction M after the absorbent body base 1 is squeezed by the processing projections of the embossing roller.

Furthermore, the linear pattern elements 1b are independently arranged so as to be linear having a predetermined length. Therefore, in spite of the absorbent body base 1 formed by being squeezed with a relatively-high linear pressure of the processing projections of the embossing roller, a difficulty in that the linear pattern elements 1b formed on the absorbent body base 1 cannot be easily peeled off from the processing projections can be prevented. This eliminates an inconvenience in that the absorbent body base 1 processed by the embossing roller is wound around the embossing roller 2, thus allowing the absorbent body base 1 to be smoothly transferred. As a result, this manufacturing method also can manufacture a absorbent body for disposable diaper having high quality with high productivity.

Here, this manufacturing method arranges the linear pattern elements 1b so as to be inclined to the orientation angle of 45 degrees to the transfer direction M. Thus, as obvious from the comparison between FIG. 7 and FIG. 4, a absorbent body for disposable diaper having almost the same effect as that by the first embodiment can be obtained by suppressing the number of the linear pattern elements 1b compared to that of the linear pattern elements 1a of the first embodiment, within the linear pattern elements 1b having substantially the same length as those of the linear pattern elements 1a of the first embodiment.

Figure 8:
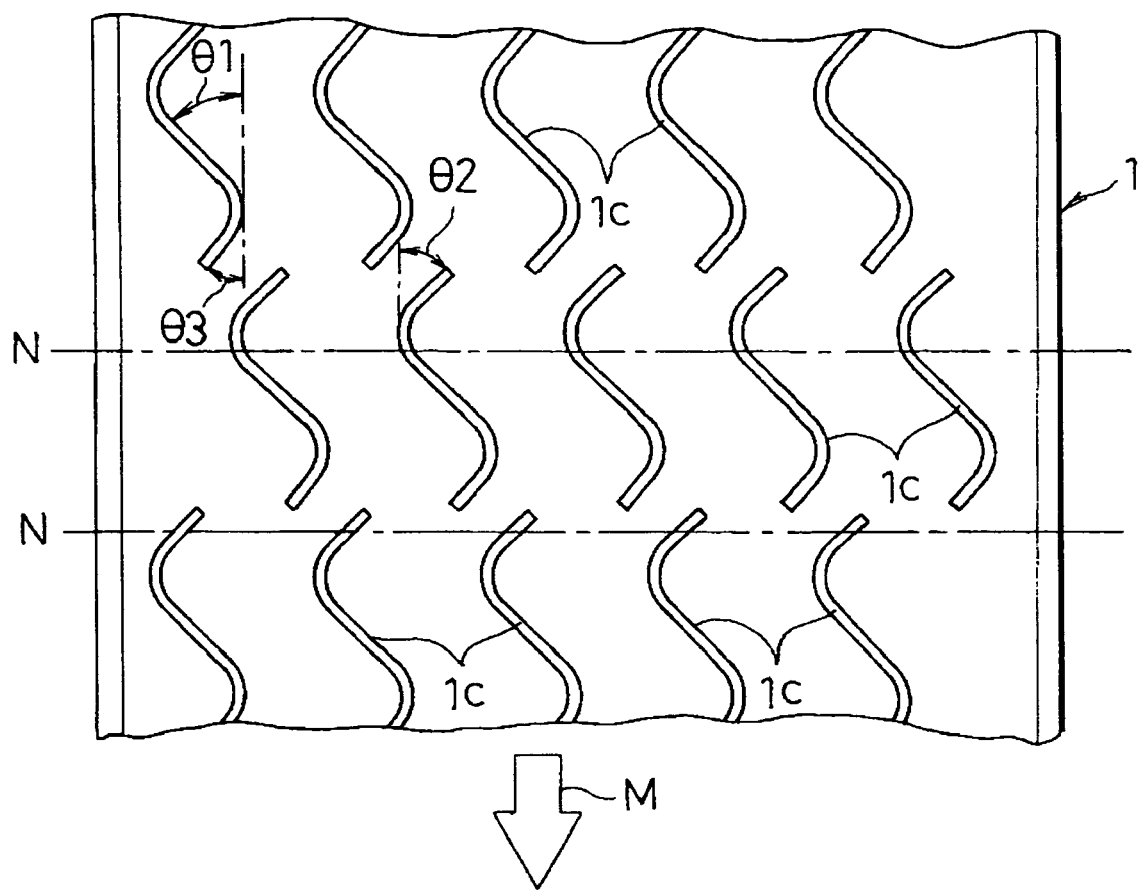
FIG. 8 This is a top view of a process for forming a linear pattern in an absorbent body base by a manufacturing method of an absorbent body according to the third embodiment of the present invention.

FIG. 8 is a top view of a process for forming linear pattern elements 1c in an absorbent body base based on a manufacturing method of an absorbent body according to the third embodiment of the present invention. The manufacturing method of this embodiment is different from the first and second embodiments only in that a plurality of linear pattern elements $1c$ formed concavely in the absorbent body base 1 have different shape and layout. Specifically, in contrast with the linear patterns having a predetermined length in the first and second embodiments, the plurality of linear pattern elements $1c$ have a shape obtained by elongating an S-shape and are arranged in a dispersed and staggered manner. The linear pattern element $1c$ is shaped so that each of orientation angles $\theta 1$, $\theta 2$, and $\theta 3$ to the transfer direction M is 50 degrees or less at the respective positions.

The manufacturing method of this embodiment can also provide substantially the same effect as those obtained by the first and second embodiments. Specifically, the same number of linear pattern elements $1c$ is provided to each of the straight lines in the width direction N (the number is five in this embodiment). Thus, a linear pressure applied from the embossing roller to the absorbent body base 1 in the width direction is always maintained uniform. Furthermore, the two neighboring linear pattern elements $1c$ in the width direction are arranged to have a fixed distance therebetween so as to be uniformly dispersed in the width direction of the absorbent body base 1. Thus, a relatively-high linear pressure can be applied to the individual processing projections of the embossing roller in a uniform and dispersed manner. As a result, the embossing roller can be always driven and rotated in a stable manner without generating vibration by variation of the pressure, since the above-described linear pressure applied from the embossing roller to the absorbent body base 1 in the width direction can be always maintained to be uniform.

Furthermore, since the linear pattern elements $1c$ are arranged with the orientation angles $\theta 1$, $\theta 2$, and $\theta 3$ that are each 50 degrees or less, in spite of a relatively high linear pressure applied from the embossing roller to the absorbent body base 1 to squeeze the absorbent body base 1, the absorbent body base 1 is prevented from having high resistance when the absorbent body base 1 is sent in the transfer direction M after the absorbent body base 1 is squeezed by the processing projections of the embossing roller. Furthermore, since the respective linear pattern elements $1c$ are independently arranged to have a distance thereamong in a staggered manner, in spite of the linear pattern elements $1b$ being formed by squeezing the absorbent body base 1 by a relatively-high linear pressure of the processing projections of the embossing roller, a difficulty in that the linear pattern elements $1b$ formed in the absorbent body base 1 cannot be easily peeled off from the processing projections can be prevented. This eliminates an inconvenience in that the absorbent body base 1 processed by the embossing roller is wound around the embossing roller 2, thus allowing the absorbent body base 1 to be smoothly transferred. As a result, this manufacturing method can also manufacture a high-quality absorbent body for disposable diaper comparable to those manufactured by the first and second embodiments, with high productivity.

Figure 9:
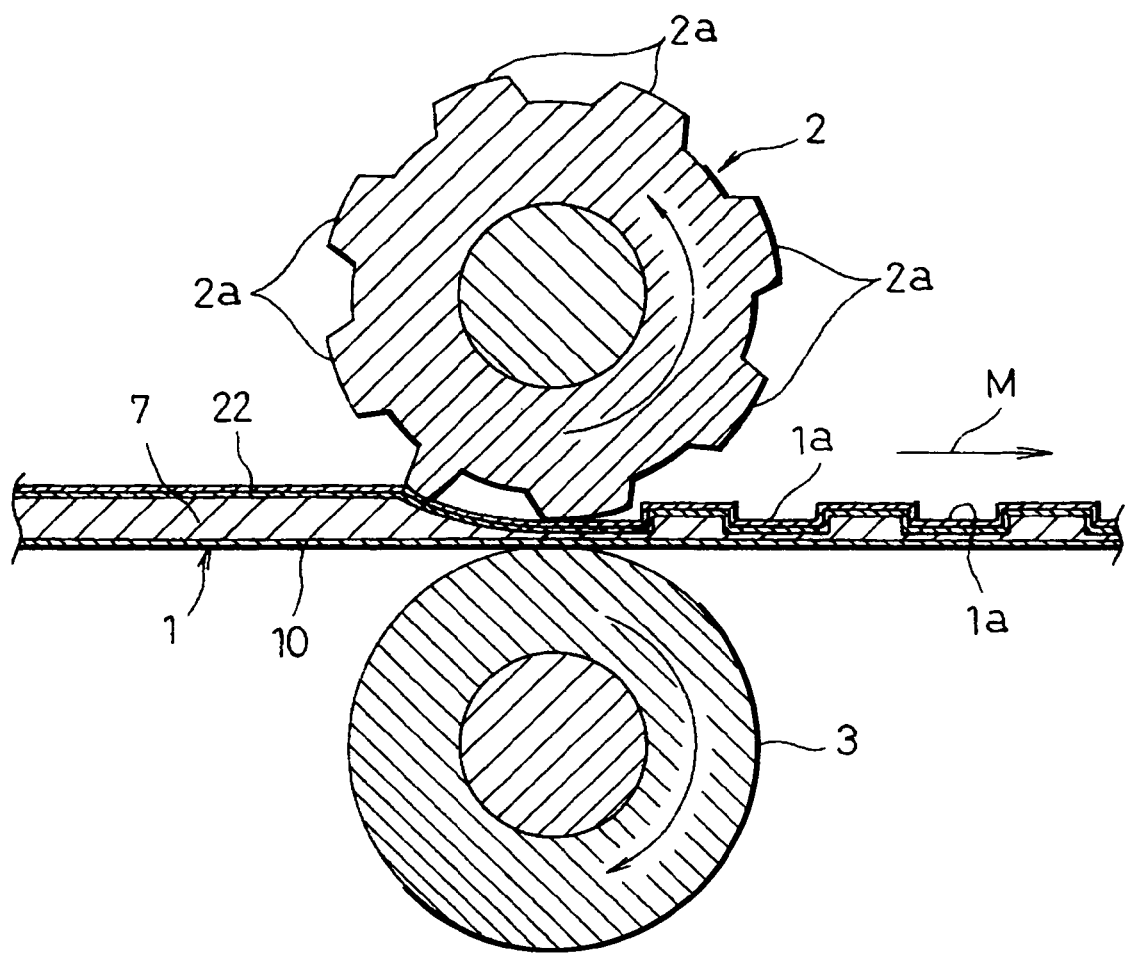
FIG. 9 This is a side sectional view illustrating a manufacturing step that embodies a manufacturing method of an absorbent body according to the fourth embodiment of the present invention.

FIG. 9 is a side sectional view illustrating a manufacturing step that embodies a manufacturing method of an absorbent body according to the fourth embodiment of the present invention. In FIG. 9, the same or similar components as those of FIG. 1 are denoted with the same reference numerals and will not be described further. In the manufacturing method of this embodiment, a face on which the linear pattern elements $1a$ are to be formed on the absorbent body base 1 is previously adhered with a liquid diffusion sheet 22 that has an appropriate thickness and includes nonwoven fabric. The absorbent body base 1 adhered with this liquid diffusion sheet 22 is sent between the embossing roller 2 and the backup plain roller 3. As a result, a face of the absorbent body base 1 has thereon the liquid diffusion sheet 22 and the linear pattern element $1a$.

Therefore, this manufacturing method can provide an absorbent body integrated with the liquid diffusion sheet 22 with high productivity while obtaining the same effect as that of the first embodiment. Furthermore, when the absorbent body obtained by this manufacturing method is used in a disposable diaper, the absorbent body provides the same effect as that obtained by the absorbent body 4 of the first embodiment. In addition, the liquid diffusion sheet 22 covering the inner surface of the absorbent body base 1 provides a capillary phenomenon to diffuse urine over the entire surface, thus preventing a situation in that the super absorbent polymer 9 (FIG. 3B) at in the particular portion of the absorbent body to have an excessive amount of urine and excessively swell.

Figure 10:
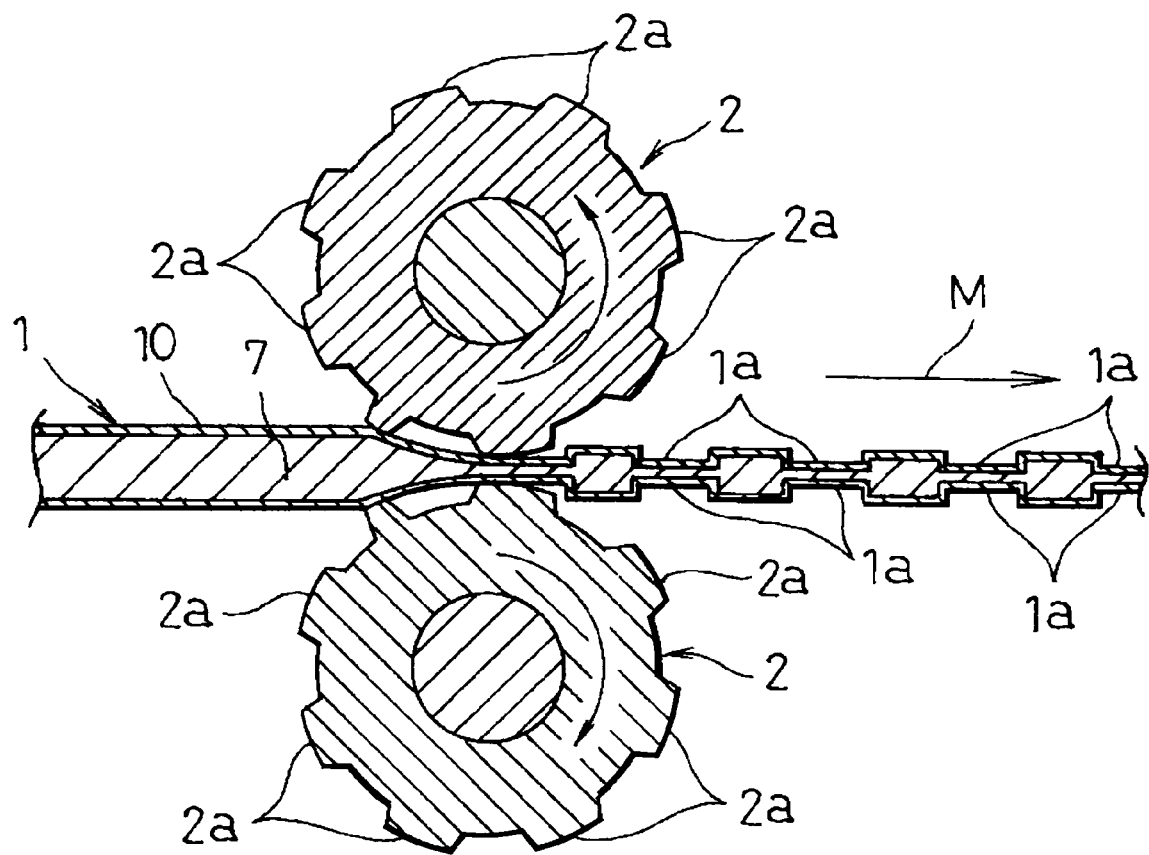
FIG. 10 This is a side sectional view illustrating a manufacturing step that embodies a manufacturing method of an absorbent body according to the fifth embodiment of the present invention.

FIG. 10 is a side sectional view illustrating a manufacturing step that embodies a manufacturing method of an absorbent body according to the fifth embodiment of the present invention. In FIG. 10, the same or similar components as those of FIG. 1 are denoted with the same reference numerals and will not be described further. The manufacturing method of this embodiment provides two embossing rollers 2, 2 shown in FIG. 1 so that these embossing rollers 2, 2 are opposed to have a predetermined distance therebetween. Then, the same absorbent body base 1 as that of the first embodiment is sent between the embossing rollers 2, 2 so that both surfaces of the absorbent body base 1 have thereon linear pattern elements $1a$ with the same layout.

In this embodiment, an absorbent body of which both surfaces of the absorbent body base 1 have thereon the linear pattern elements $1a$ with the same layout can be manufactured with high productivity, while obtaining the same effect as that obtained by the first embodiment. When the absorbent body obtained by this manufacturing method is used in a disposable diaper, the absorbent body provides the same effect as that obtained by the absorbent body 4 of the first embodiment and can also provide a further higher strength by the pairs of linear pattern elements $1a$ formed on both surfaces of the absorbent body base 1 so as to be opposed to each other.

INDUSTRIAL APPLICABILITY

The manufacturing method of an absorbent body according to the present invention can manufacture, with high productivity, an absorbent body that has an absorbent element having a predetermined thickness while securely providing an intended absorption performance, and also has a strength by which a diaper including the absorbent body is prevented from losing its shape even when the absorbent element sufficiently absorbs water and swell. When the absorbent body obtained by this manufacturing method is used as a main component of a disposable diaper, a favorable disposable diaper having required absorption performance and strength can be obtained.

DESCRIPTION OF REFERENCE NUMERALS

1 Absorbent body base
$1a$, $1b$, and $1c$ Linear pattern
2 Embossing roller (press print processing roller)
$2a$ Processing projection
3 Backup plain roller (roller)
4 Absorbent body for disposable diaper
7 Absorbent element 8 Pulp
9 Super absorbent polymer
10 Storage bag
22 Liquid diffusion sheet
M Transfer direction
N Straight line

The invention claimed is:

1. A manufacturing method for manufacturing an absorbent body, comprising:
   transferring a stripe-shaped absorbent body base, including an absorbent element obtained by mixing at least pulp with super absorbent polymer, through a pair of rollers that are provided to be opposed to each other with a predetermined distance therebetween, wherein at least one of the rollers is a press print processing roller that has a plurality of processing projections with a predetermined layout on a circumference surface;
   forming a plurality of linear pattern elements on at least one surface of the absorbent body base, wherein the linear pattern elements are formed by being squeezed by the processing projections so as to have a groove-like shape, and wherein the plurality of linear pattern elements are individually spaced from one another and dispersed in a staggered manner; and
   cutting the absorbent body base to have a predetermined size after the linear pattern elements are formed,
   wherein the linear pattern elements are formed in a shape so that an orientation angle, which is a degree of inclination of the linear pattern elements to a transfer direction of the absorbent body base, is 50 degrees or less at any portion; and
   wherein the plurality of linear pattern elements are arranged in straight lines so that a constant number of the linear pattern elements are formed on any of the straight lines extending in a width direction orthogonal to the transfer direction of the absorbent body base, the straight lines being defined anywhere along the transfer direction of the absorbent body base, and wherein distances between each of the constant number of the linear pattern elements in the width direction are equal to one another.

2. The manufacturing method according to claim 1, wherein the press print processing roller forms the linear pattern elements by squeezing the absorbent body base with a linear pressure of 5.56 to 13.89 kgf/cm.

3. An absorbent body for a disposable diaper manufactured by the manufacturing method of claim 1, wherein:
   the absorbent element is filled into a storage bag obtained by sealing edge parts of a liquid-permeable sheet of the absorbent body base provided with the linear pattern elements;
   the plurality of linear pattern elements have the groove-like shape when seen from top and are arranged in the dispersed and staggered manner to have spaces thereamong; and
   an area in the absorbent body base in which the linear pattern elements are not formed has a thickness of 3 mm or less.

4. The absorbent body for the disposable diaper according to claim 3, wherein the linear pattern elements are formed in an S-shape so that each of orientation angles to the transfer direction is 50 degrees or less at respective positions, and the linear pattern elements are arranged in the dispersed and staggered manner.

5. The absorbent body for the disposable diaper according to claim 3, wherein the linear pattern elements are inclined to either right or left directions with an orientation angle of substantially 45 degrees to the transfer direction of the absorbent body base, and
   wherein pattern rows of the plurality of linear pattern elements intermittently arranged with a first inclination direction along the transfer direction having a fixed distance thereamong are arranged in the width direction orthogonal to the transfer direction, and pattern rows having a second inclination direction are alternately provided along the width direction, and wherein respective two neighboring pattern rows in the width direction are arranged so that each pattern row is dislocated by a distance between the linear pattern elements neighboring in the transfer direction.

6. The manufacturing method according to claim 1, wherein each of plurality of the linear pattern elements are formed in a linear shape.

7. The manufacturing method according to claim 1, wherein each of the plurality of processing projections are projected in a linear shape, and wherein the plurality of processing projections are individually spaced from one another and are disposed in a staggered manner.

* * * * *